(12) United States Patent
Liu et al.

(10) Patent No.: US 10,520,460 B2
(45) Date of Patent: Dec. 31, 2019

(54) METHOD FOR DETERMINING DIFFUSION

(71) Applicant: Cilag GmbH International, Zug (CH)

(72) Inventors: Zuifang Liu, Inverness (GB);
Magdalena Gutowska, Inverness (GB)

(73) Assignee: LifeScan IP Holdings, LLC, Malvern, PA (US)

( * ) Notice: Subject to any disclaimer, the term of this patent is extended or adjusted under 35 U.S.C. 154(b) by 22 days.

(21) Appl. No.: 15/518,944

(22) PCT Filed: Oct. 26, 2015

(86) PCT No.: PCT/EP2015/074721
§ 371 (c)(1),
(2) Date: Apr. 13, 2017

(87) PCT Pub. No.: WO2016/066575
PCT Pub. Date: May 6, 2016

(65) Prior Publication Data
US 2017/0241940 A1    Aug. 24, 2017

(30) Foreign Application Priority Data

Oct. 27, 2014   (GB) ................................. 1419113.4

(51) Int. Cl.
*G01N 27/327*    (2006.01)
*G01N 27/48*    (2006.01)

(52) U.S. Cl.
CPC ..... *G01N 27/3274* (2013.01); *G01N 27/3272* (2013.01); *G01N 27/48* (2013.01)

(58) Field of Classification Search
CPC . G01N 27/3274; G01N 27/48; G01N 27/3272
See application file for complete search history.

(56) References Cited

U.S. PATENT DOCUMENTS 5,942,102 A    6/1999   Hodges et al.
7,955,492 B2   6/2011   Fujiwara et al.
(Continued)

FOREIGN PATENT DOCUMENTS

CN    1938590 A      3/2007
CN    103575782 A    2/2014
(Continued)

OTHER PUBLICATIONS

"Experiments in Analytical Electrochemistry: 3. Chronoamperometry With a Planar Solid Electrode", online webpage, accessed from http://www.asdlib.org/onlineArticles/elabware/kuwanaEC_lab/PDF-21-Experiment3.pdf, 7 pages, published Jan. 9 (Year: 2011).*
(Continued)

*Primary Examiner* — J. Christopher Ball

(57) ABSTRACT

A method for determining a diffusion feature of a fluidic sample using redox reactions in an electrochemical cell that has at least two electrodes, wherein the first electrode has at least one redox mediator at its surface or in close vicinity of its surface, and the second electrode has an electrode surface free of the redox mediator(s) in the beginning of a test, the method comprising: applying an electric potential to a fluidic sample in the electrochemical cell to initiate redox reactions at the two electrode surfaces; measuring current associated with the applied potential as a function of time, and using a measurement point on a transient part of the measured current at or after a turning point and its associated time to determine the diffusion feature.

15 Claims, 4 Drawing Sheets

(56) References Cited

U.S. PATENT DOCUMENTS

| | | | |
|---|---|---|---|
| 8,016,997 B2 | 9/2011 | Diamond et al. | |
| 2002/0125145 A1 | 9/2002 | Ohara et al. | |
| 2006/0231421 A1* | 10/2006 | Diamond | C12Q 1/006 205/777.5 |
| 2007/0138026 A1 | 6/2007 | Fujiwara et al. | |
| 2009/0184004 A1 | 7/2009 | Chatelier et al. | |
| 2013/0071869 A1 | 3/2013 | Wu | |
| 2013/0284611 A1 | 10/2013 | Matzinger | |
| 2013/0306493 A1 | 11/2013 | Chatelier et al. | |
| 2014/0021046 A1 | 1/2014 | Huang et al. | |

FOREIGN PATENT DOCUMENTS

| | | | |
|---|---|---|---|
| EP | 1839571 A1 | 10/2007 | |
| JP | 2009168815 A | 7/2009 | |
| JP | 2014504722 A | 2/2014 | |
| RU | 2305279 C2 | 8/2007 | |
| WO | 9700441 A1 | 1/1997 | |
| WO | 9718464 A1 | 5/1997 | |
| WO | 2004113913 A1 | 12/2004 | |
| WO | 2005054840 A1 | 6/2005 | |
| WO | 2005103669 A1 | 11/2005 | |
| WO | 2006109278 A2 | 10/2006 | |
| WO | 2006109279 A2 | 10/2006 | |
| WO | 2009108239 A2 | 9/2009 | |
| WO | 2014037745 A1 | 3/2014 | |

OTHER PUBLICATIONS

International Search Report and Written Opinion issued in corresponding International Patent Application No. PCT/EP2015/074721, dated Jan. 5, 2016, 12 pages.

First Office Action issued in corresponding Chinese Patent Application No. 201580058607Z, dated Dec. 25, 2018, 24 pages. (with English translation).

Search Report issued in corresponding United Kingdom Application No. GB1419113.4, dated Apr. 10, 2015, 3 pages.

Notice of Reasons for Rejection issued in corresponding Japanese Patent Application No. 2017-514641, dated May 21, 2019, 5 pages. (with English translation).

Decision on Grant and Search Report issued in correspondence Russian Patent Application No. 2017-118328, dated Apr. 16, 2019, 19 pages.

Examination Report issued in corresponding Taiwanese Patent Application No. 104135211, dated Mar. 12, 2019, 4 pages. (with English translation).

Examination Report issued in corresponding European Patent Application No. 15786914Z, dated Jun. 28, 2018, 4 pages.

* cited by examiner

METHOD FOR DETERMINING DIFFUSION

PRIORITY

This application is the National Stage under Section 371 of International Patent Application PCT/EP2015/074721 filed on Oct. 26, 2015, which application claims the benefits of priority of prior filed United Kingdom Patent Application Serial No. 1419113.4 filed on Oct. 27, 2014, which prior applications are hereby incorporated by reference as if fully set forth herein.

FIELD OF THE INVENTION

The present invention relates to a method and device for determining diffusion of a fluidic sample using redox reactions in an electrochemical cell. The invention also relates to a method and device for simultaneously determining diffusion and the contribution of redox-active substance(s) in a fluidic sample using redox reactions.

BACKGROUND OF THE INVENTION

Electrochemical-based sensors (e.g. self-monitoring blood glucose strips) are used for measuring analyte in fluid samples (e.g. whole blood). However, their accuracy can suffer from diffusion interfering factors (DIF) which affect analyte mass transfer in the test fluids, e.g. blood haematocrit (Hct) because red blood cells block the diffusion pathway of the analyte (e.g. glucose). Another factor negatively impacting the sensor accuracy is redox interfering factors (RIF) which result from any redox-active substance(s) that undergoes redox reactions and hence, generates interfering signals (e.g. uric acid interferes with electrochemical glucose measurement).

Technologies mitigating DIF are known. These use an active approach which relies on obtaining DIF sensitive signals, which are used to correct/compensate DIF. Examples of active DIF mitigation are described in US2002125145A1, US20090184004A1 and U.S. Pat. No. 8,016,997B2. These methods for DIF mitigation rely on determining diffusion between the two electrodes across the strip sample chambers. Hence, they can suffer from strip-to-strip variations in the sample chamber height.

Technologies mitigating RIF are known. Again, these use an active approach relying on obtaining RIF sensitive signals, which are for correction/compensation. Examples of active RIF mitigation for self-monitoring blood glucose are described in US2002125145A1 and WO2014037745A1.

The above mentioned technologies address only DIF or RIF, or separately address DIF and RIF using different techniques/methods.

Mitigation of both DIF and RIF to meet product accuracy requirements is essential. There is a need for improved techniques for achieving this mitigation.

SUMMARY OF THE INVENTION

This invention is concerned with a technology for simultaneously determining diffusion and redox-active substance(s) in fluidic samples. The technology holds potential for a variety of applications. For instance, the measured diffusion and redox-active substance(s) can be used for active mitigation of both DIF and RIF in electrochemical measurements of analytes, for example glucose. By diffusion interfering factor (DIF), it is meant a property of a fluidic sample affecting mass transfer, for example blood Hct, viscosity, diffusion coefficient. By redox interfering factor (RIF), it is meant any redox-active substance(s) that undergoes redox reactions and hence, generates interfering signals.

According to one aspect of the invention, there is provided a method of determining diffusion of a fluidic sample using redox reactions in an electrochemical cell that has at least two electrodes, wherein the first electrode has at least one redox mediator at its surface or in close vicinity of its surface, and the second electrode has an electrode surface free of the redox mediator(s) at the beginning of a test, the method comprising: applying an electric potential to a fluidic sample in the electrochemical cell to initiate redox reactions at the two electrode surfaces; measuring current associated with the applied potential, and using the measured current and its associated test time to determine a diffusion property or characteristic.

The method may further involve using the measured current and its associated test time to determine a contribution by a redox-active substance. By redox-active substance, it is meant a substance present in a test sample, which generates interfering signals by undergoing redox reactions at an electrode under an applied electric potential and/or reacting with the redox mediator to change the redox state of the mediator, which then undergoes redox reaction at the electrode (for example uric acid in a blood sample).

The method may further involve using calibration information together with the measured current and its associated test time to determine the diffusion property or characteristic.

The diffusion property or characteristic may be associated with mass transfer in a fluidic sample, including diffusion coefficient, haematocrit, viscosity.

The redox-active substance may be at least one substance which undergoes redox reaction at the second electrode under the applied potential.

The potential may have a constant magnitude, or a varying magnitude with time, or combination of a constant magnitude and a varying magnitude.

The current may be a single value of the measured current, or an average value of consecutive measured currents over a duration of 0.5 second, preferably 0.1 second, more preferably 0.03 second.

The electrodes may be configured in a co-facial manner such that the two electrode surfaces are spatially arranged facing each other with a minimum face-to-face distance of 10 to 1000 microns, preferably 35 to 500 microns, and more preferably 50 to 120 microns.

The electrodes may be configured in a co-planar manner such that the two electrode surfaces are spatially arranged in the same plane with the minimum edge-to-edge distance of 10 to 2000 microns, preferably 50 to 900 microns, and more preferably 100 to 500 microns.

According to another aspect of the invention, there is provided a meter or device for determining a diffusion feature of a fluidic sample using redox reactions in an electrochemical cell that has at least two electrodes, wherein the first electrode has at least one redox mediator at its surface or in close vicinity of its surface, and the second electrode has an electrode surface free of the redox mediator(s) in the beginning of a test, the meter or device being configured to: apply an electric potential to a fluidic sample in the electrochemical cell to initiate redox reactions at the two electrode surfaces; measure current associated with the applied potential as a function of time; and use a measurement point on a transient part of the measured current at or after a turning point and its associated time to determine the diffusion feature.

The turning point may be the point at which a first transient part ends and a second transient part begins, wherein the first transient part deviates from a Cottrell current decay and the second transient part substantially follows a Cottrell current decay.

The meter or device may be configured to identify the turning point on the transient part of the measured current. The meter or device may be configured to use the identified turning point to determine the measurement point that is to be used for determining the diffusion feature, wherein the measurement point is offset in time from the turning point ($t_{turn}+\Delta t$, =measurement point).

The meter or device may be configured to use the measurement point current and its associated test time to determine simultaneously the diffusion feature and contribution of at least one redox-active substance.

The meter or device may be configured to store calibration information and use the calibration information together with the measurement point in the measured current and its associated test time to determine the diffusion feature.

The meter or device may be configured to store a function that relates a test time and the diffusion feature and use the function together with the measurement point current test time to determine the diffusion feature.

The diffusion feature may be a diffusion property or characteristic associated with mass transfer in a fluidic sample, including diffusion coefficient, haematocrit, viscosity.

The redox-active substance is at least one substance which undergoes redox reaction at the second electrode under the applied electric potential.

The meter or device may be configured to apply an electric potential that has a constant magnitude, or a varying magnitude with time, or a combination of a constant magnitude and a varying magnitude.

The meter or device may be configured to measure a single current value of at each measurement point or an average value of consecutive measured currents over a duration of 0.5 second, preferably 0.1 second, more preferably 0.03 second.

BRIEF DESCRIPTION OF THE DRAWINGS

Various aspects of the invention will now be described by way of example only, and with reference to the following drawings, of which:

FIG. 3b is a box plot of $t_{turn}$ versus Hct data of FIG. 3a, and

DETAILED DESCRIPTION OF THE DRAWINGS

Figure 1:
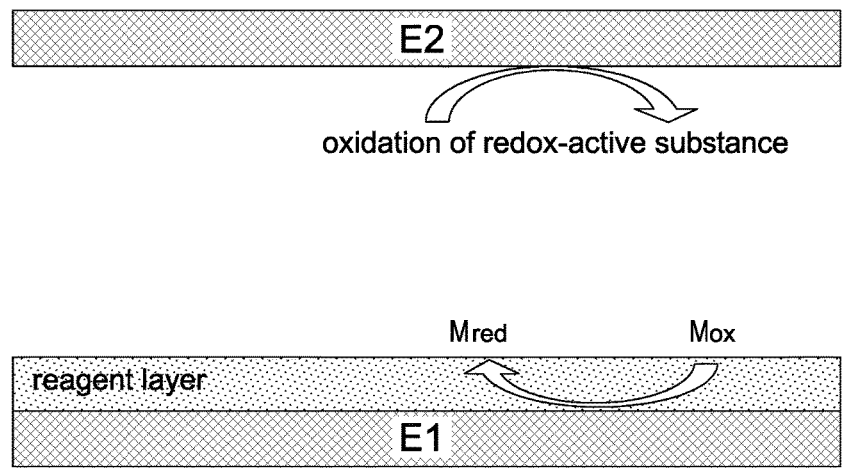
FIG. 1 shows a redox reaction at two electrodes stimulated by applying an electrical potential between the electrodes.

FIG. 1 shows redox reactions of an electrochemical test strip, for example a self-monitoring blood glucose strip. The strip has two electrodes, a first electrode E1 and second electrode E2. The first electrode E1 is covered with a reagent layer which contains redox mediator (M) and other materials (e.g. enzyme) while the second electrode E2 has a surface without the covering reagent layer. The first and second electrodes E1 and E2 respectively are electrically connected to a potentiostat (not shown). In use, the first and second electrodes E1 and E2 respectively are in contact with a whole blood sample and an electric potential (voltage) is applied between the two electrodes. This results in redox reactions at the both electrodes. The resulting current between the first and second electrodes E1 and E2 is measured as a function of time.

To test the strip, an electric potential is applied between the first and second electrodes E1 and E2, and the current flow is measured. The magnitude and polarity of the electric potential are chosen to initiate a reduction(s) of the mediator(s) at the first electrode E1 and an oxidation(s) of redox-active substance(s) at the second electrode E2. Applying a blood sample to the strip sample chamber triggers physical and chemical processes/changes which depend on Hct and redox-active substance(s) of the blood sample. The physical processes include hydration of the reagent layer, dissolution of the mediator, and double-layer charging (a process to neutralize the charge imbalance near the electrode surfaces by rearrangement of charged species in the blood). The chemical processes include oxidation(s) of the redox-active substance(s) at the second electrode E2 and reduction of the oxidised mediator $M_{ox}$ at the first electrode E1, as shown in FIG. 1.

Figure 2:
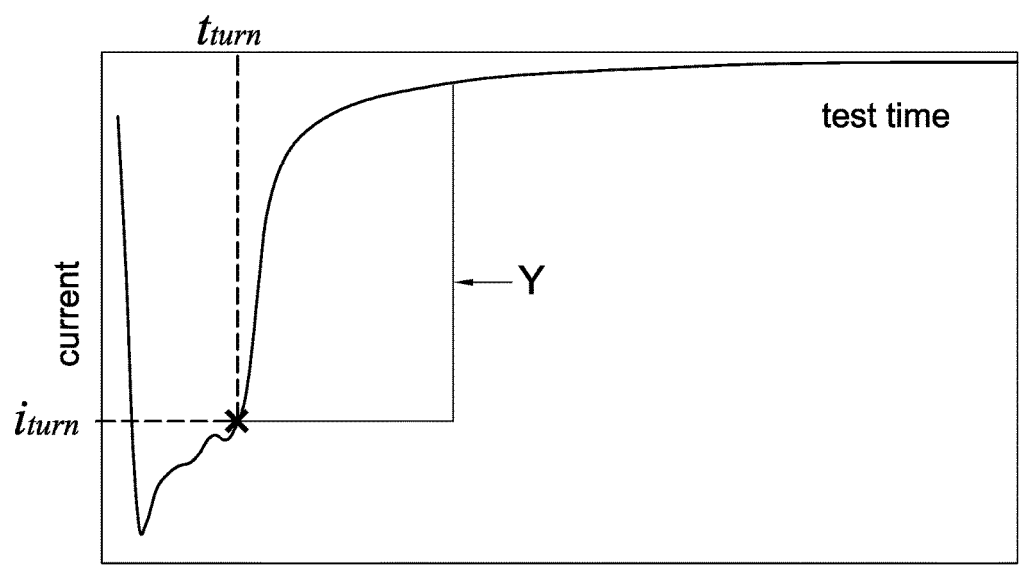
FIG. 2 shows a plot of current versus time for the device of FIG. 1 measured after application of the electrical potential, on which a turning point at time $t_{turn}$ and current $i_{turn}$ are shown.

As a result of the physical and chemical processes, the recorded current has a transient that has a unique pattern which deviates from Cottrell current decay. This is shown in FIG. 2. Each current transient has a "turning-point", as marked "X" in FIG. 2, which defines a current parameter $i_{turn}$ and a time parameter $t_{turn}$. The turning point is the point at which a first transient part with low level oscillations ends, and a second transient part with a smooth current decay begins (NB in FIG. 2 the current shown is a negative current and so the rising slope to the right of the low level oscillations represents a current decay). The first transient part deviates from Cottrell current decay while the second transient part substantially follows Cottrell current decay. The second transient part ends as soon as the current reaches a steady state or the redox mediator arrives at the second electrode E2 by diffusion from the reagent layer. The turning point may be identified by a process(es)/algorithm(s) which may be developed using various mathematical approaches/techniques.

The deviation of the current transient from Cottrell current decay, in particular the first transient part, mainly results from the physical processes that play a predominant role at this stage in changing the active surface area of the first electrode E1 and/or availability of the mediator for the reduction at the first electrode E1. These physical processes are dependent on diffusion of the blood sample and independent of the redox-active substance(s) concentration. Therefore, the time at which the transient current transitions from the first transient part to the second transient part, $t_{turn}$, is a function of diffusion.

At an early stage of a strip test, the reduced mediator has not diffused across the sample chamber to reach the surface of the second electrode E2. Hence, the oxidation current is predominantly generated by the oxidation of redox-active substance(s). At the same time, the oxidation of redox-active substance(s) is dependent on mass transfer of the redox-active substance(s) in the fluidic sample. Therefore, $i_{turn}$ is a function of both the redox-active substance(s) and its diffusion.

The function for $t_{turn}$ and the function for $i_{turn}$ may be derived from laboratory data obtained by testing fluidic samples with designated diffusion property and redox-active substance(s). In the present invention, testing a fluidic sample with an electrochemical cell, recording the current transient, identifying the turning point, defining $t_{turn}$ and $i_{turn}$, and solving the two functions/equations enables simultaneous determinations of diffusion and the contribution/impact of redox-active substances of the fluidic sample.

The determination/measurement refers to quantitative, semi-quantitative, or qualitative evaluation of a diffusion property of the test sample (e.g. Hct) or a redox-active substance(s) (e.g. uric acid) in the test sample. For quantitative and semi-quantitative evaluation, the result is a numerical representation of the signal generated by one or more of the diffusion property or the redox-active substances present in the test sample. As a measure of the redox-active substance(s), it quantifies overall contribution of the redox-active substances.

The method is also applicable to simultaneously measuring diffusion and any redox-active substance(s) which undergoes reduction at the second electrode E2. In this case, the reagent layer at the first electrode E1 contains mediator in its reduced state and an electric potential is applied to initiate a reduction(s) of the redox-active substance(s) at the second electrode E2.

To allow diffusion dependent features or features that have an impact on diffusion to be measured in accordance with the invention, the diffusion feature of interest has to be calibrated as a function of the turning time $t_{turn}$. Alternatively, the diffusion feature of interest could be represented by a mathematical function that is dependent on the turning time $t_{turn}$. In either case, once the relationship between the diffusion feature and the turning time $t_{turn}$ is known, it can be used in later measurements to provide a measure of the diffusion feature. The diffusion feature may be, for example, diffusion coefficient, haematocrit (which impacts diffusion), coagulation or viscosity.

To allow the contribution of any redox-active substance(s) to be measured, the redox-active substance(s) of interest has to be calibrated as a function of the turning time $t_{turn}$ and additionally as a function of turning current $i_{turn}$. Alternatively, the redox-active substance(s) of interest could be represented by a mathematical function that is dependent on the turning time $t_{turn}$ and the turning current $i_{turn}$. In either case, once the relationship between the redox-active substance(s), the turning time $t_{turn}$ and the turning current $i_{turn}$ is known, it can be used in later measurements to provide a measure of the redox-active substance(s) or of the contribution to the measured current made by the redox-active substance(s).

The measure of the redox-active substance(s) may be a measure of the substance concentration in the sample. The measure of the contribution made by the redox-active substance(s) may be a measure of the contribution to the current. This can be used in subsequent steps or processes to correct any calculations based on the current measurements, when such calculations require the effects of the redox-active substance(s) to be excluded. For example, uric acid interferes with electrochemical glucose measurements, and the invention would allow the effects of the uric acid to be identified and excluded from any calculation of glucose levels.

The methodology of the invention has been tested using commercially available strips. Tests were done at room temperature. A potential of −400 mV was applied and the resultant current signals recorded. Two blood samples were used from two different donors, each with a different glucose level. The samples were 2×6×4 (glucose/donor×Hct×uric acid) manipulated venous blood. The tests were repeated eight to ten times for each blood sample. The results of these tests are represented graphically in FIGS. 3a, 3b and 4.

Figure 3A:
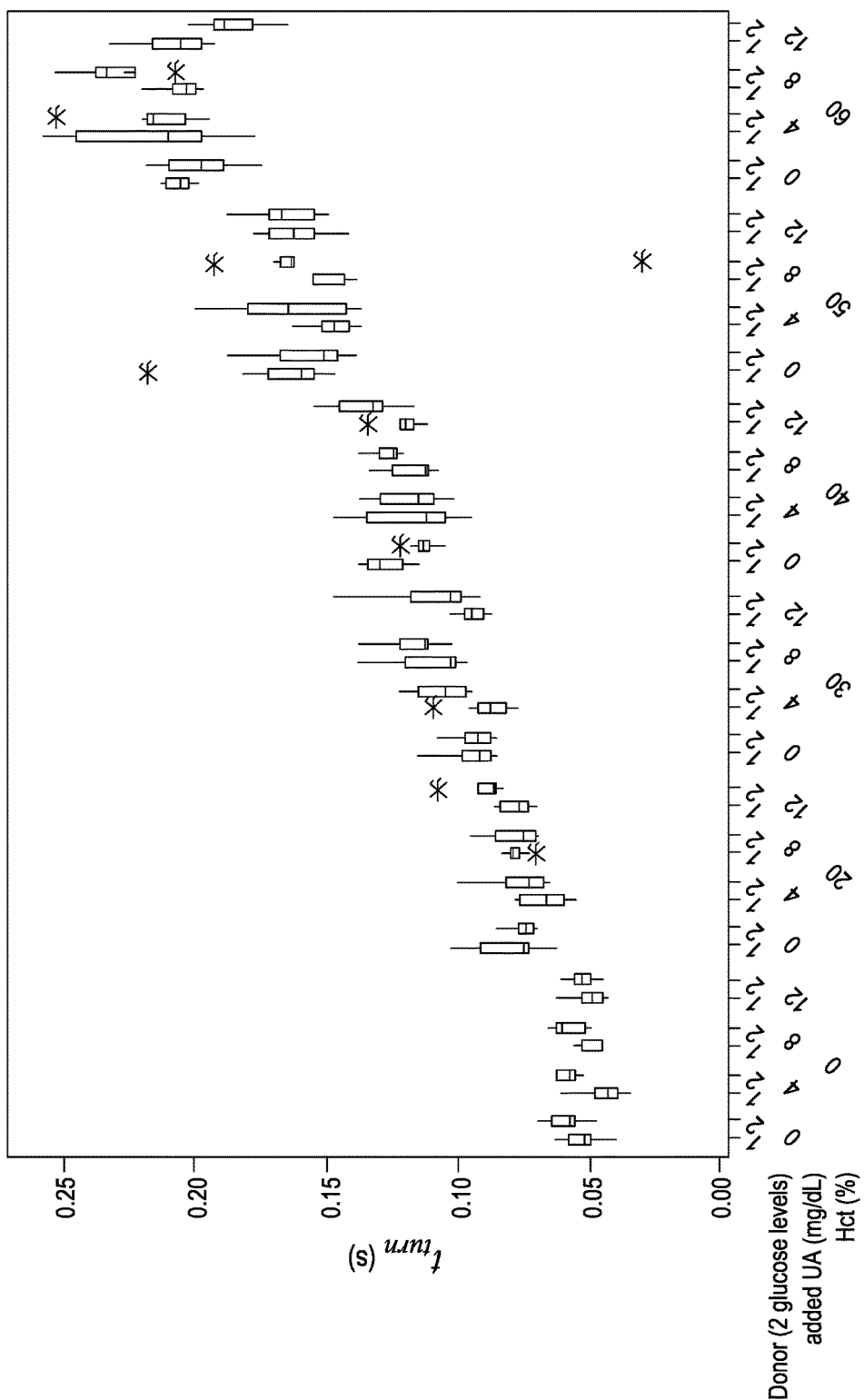
FIG. 3a is a box plot of $t_{turn}$ versus glucose, uric acid and Hct for blood samples of two donors.
Figure 3B:
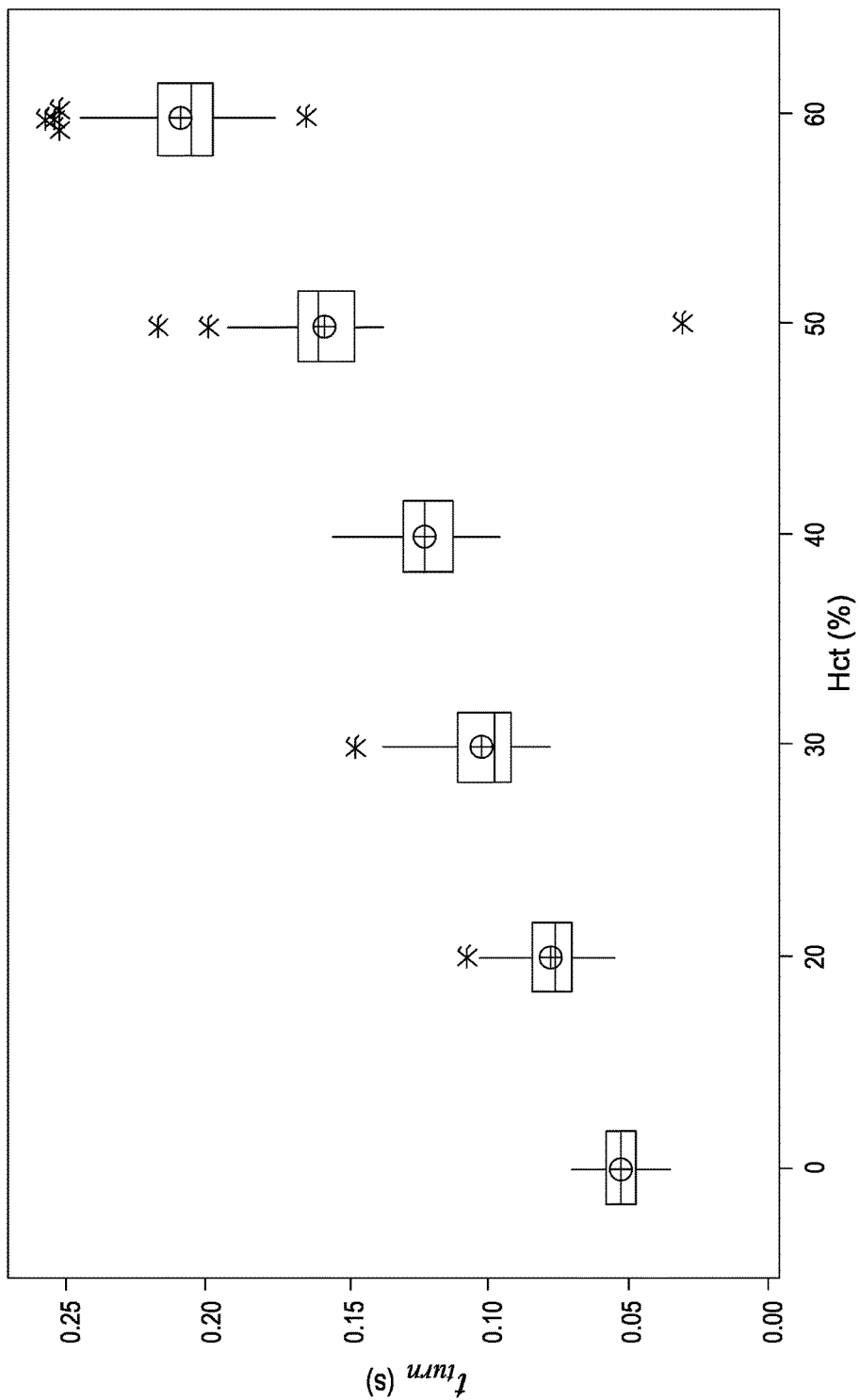

FIG. 3a is a box plot of $t_{turn}$ versus various blood sample variables, including glucose concentration, spiked/added uric acid concentration (a redox-active substance that interferes with the glucose measurement) and Hct (which impacts diffusion). In this example, samples from two different donors were used, so that samples with two different glucose concentrations could be tested (on the x-axis of FIG. 3a "1" and "2" are for Donor1 and Donor2 respectively). In this case, the glucose concentrations were approximately 75 mg/dL for Donor1 and 125 mg/dL for Donor2. The native (before spiking) uric acid concentrations were 4.47 mg/dL for Donor1 and 4.79 mg/dL for Donor2 respectively. FIG. 3b is a box plot of $t_{turn}$ versus Hct. This shows the same Hct data as in FIG. 3a, but without the glucose and uric acid data for clarity.

FIGS. 3a and 3b clearly indicate a strong correlation between $t_{turn}$ and Hct with a good resolution, whilst glucose and uric acid have little effect on $t_{turn}$. A mathematical calibration equation can be derived from the data (e.g. those in FIG. 3b) and used to provide a measurement of diffusion d or a diffusion related property (e.g. Hct) upon testing a fluidic sample. The calibration equation can be expressed as:

$$t_{turn}=f(d) \quad [1]$$

Figure 4:
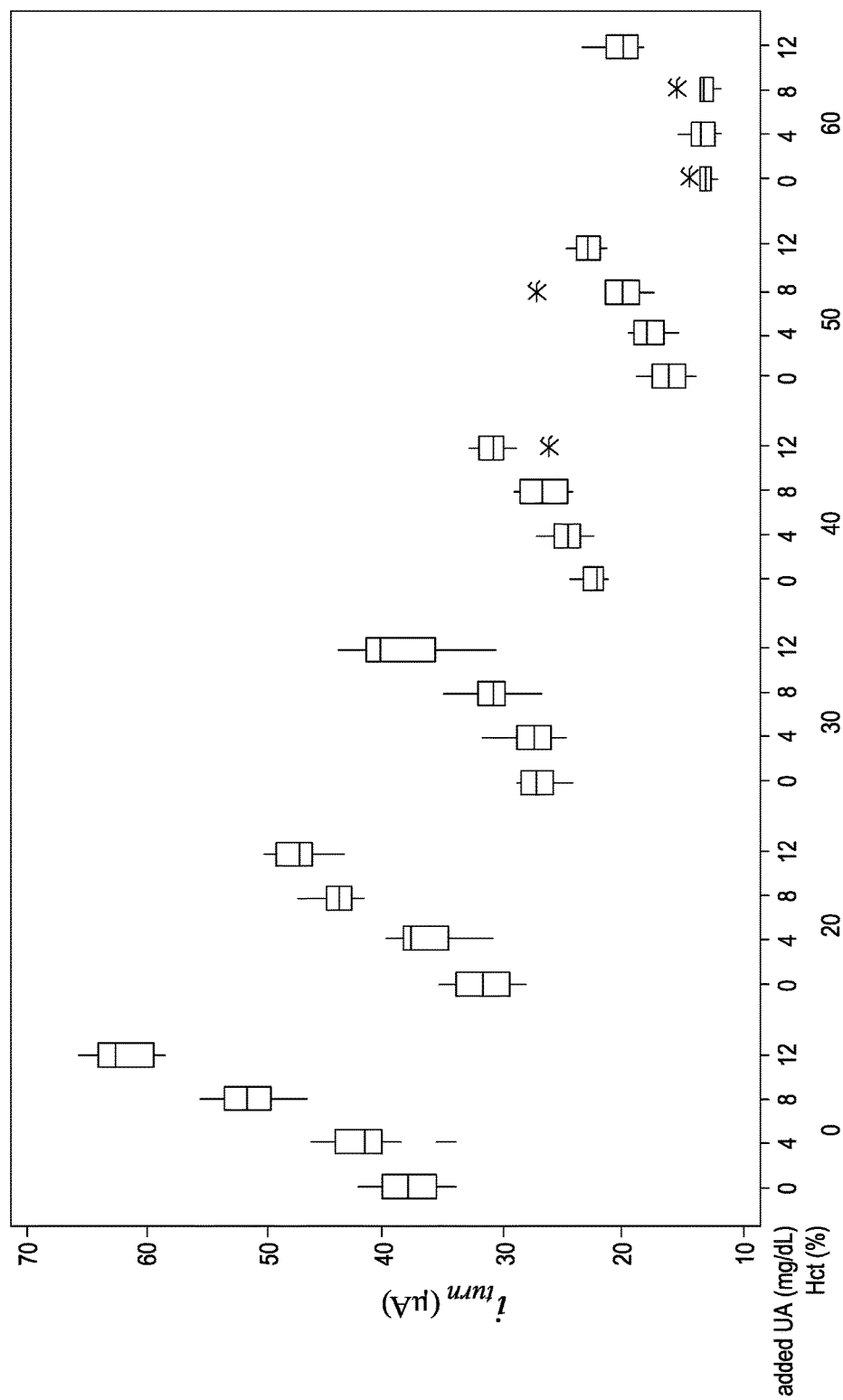
FIG. 4 is a box plot of $i_{turn}$ versus Hct and uric acid concentration at a glucose concentration around 75 mg/dL.

FIG. 4 is a box plot of $i_{turn}$ versus Hct and uric acid concentration at a glucose concentration around 75 mg/dL (Donor1 data). The plot clearly indicates a strong correlation between $i_{turn}$ and Hct with a good resolution. The plot also indicates a clear correlation between $i_{turn}$ and uric acid concentration at different Hct levels. A mathematical calibration equation can be derived from laboratory data (e.g. those in FIG. 4). The calibration equation can be expressed as:

$$i_{turn}=f(d,r) \quad [2]$$

Measurements of diffusion d or a diffusion related property (e.g. Hct) and the contribution of redox-active substance(s) r (e.g. uric acid) can be obtained by solving equations [1] and [2]. Where multiple redox-active substances are present, the contribution determined may be a measure of the current that is attributable to more than one redox-active substance. This measure may be used as a correction factor for any measurements/calculations that are dependent on current. Where only a single redox-active substance is present, equations [1] and [2] can be used to determine the concentration of the redox-active substance in the fluid sample.

The invention has been described with reference to identifying the current and time parameters at the "turning-point". However, a current parameter and/or a time parameter can be obtained from the other parts of the current transient, in particular after the "turning-point". For example, a current parameter and a time parameter could be used from the section of the current response marked Y in FIG. 2. Indeed any current and associated time parameter from the second transient part could be used.

An advantage of using the turning point is that the current and time can be easily identified using simple processing techniques. If current and time parameters away from the turning point are used, their location could be identified with reference to the turning point. For example, if it were decided that the optimum current and time parameters were at a time $t_{turn}+\Delta t$, then the parameters could be identified by firstly identifying $t_{turn}$ and using this as a reference to identify the time $t_{turn}+\Delta t$.

The present invention provides a simple and effective technique for measuring both diffusion (e.g. Hct) and the contribution/impact of redox-active substance(s) (e.g. interference) in fluidic samples (e.g. blood) at the same time. It can be used for a variety of applications (e.g. Hct, viscosity, coagulation, etc.). It can also be used to determine correction factors to improve the accuracy of self-monitoring blood glucose tests by mitigating DIF (e.g. Hct) and RIF (e.g. uric acid), which are the two major error sources for episodic blood glucose monitoring. In this case, the methodology of the invention is independent of the glucose concentration in the blood samples. Hence, it is more reliable and robust than many prior art techniques. A further advantage is that there are no fundamental limitations on the strip sample chamber height, thereby reducing measurement errors resulting from the strip-to-strip and/or batch-to-batch variations.

A skilled person will appreciate that variations of the disclosed arrangements are possible without departing from the invention. For example, although the invention has been described with reference to a test strip with only two electrodes, the invention could equally be applied to strips with three or more electrodes. Also, whilst the test strip of FIG. 1 has parallel plate electrodes (i.e. co-facial electrode configuration), the invention is applicable to strips with co-planar electrode configuration, i.e. all the electrode surfaces are in the same plane. In addition, although the signal of FIG. 2 is a response to a potential that has a constant magnitude, the applied potential could have a magnitude that varies with time, or could have a combination of a constant magnitude and a varying magnitude. Accordingly the above description of the specific embodiment is made by way of example only and not for the purposes of limitation. It will be clear to the skilled person that minor modifications may be made without significant changes to the operation described.

The invention claimed is:

1. A method for determining a diffusion feature of a fluidic sample using redox reactions in an electrochemical cell that has at least two electrodes, wherein the first electrode has at least one redox mediator at its surface or in close vicinity of its surface, and the second electrode has an electrode surface free of the at least one redox in the beginning of a test, the method comprising:
applying an electric potential to a fluidic sample in the electrochemical cell to initiate redox reactions at the two electrode surfaces;
measuring current associated with the applied potential as a function of time, and
using a measurement point on a transient part of the measured current at or after a turning point and its associated time to determine the diffusion feature;
wherein the turning point is the point at which a first transient part ends and a second transient part begins, wherein the first transient part deviates from a Cottrell current decay and the second transient part substantially follows a Cottrell current decay;
identifying the turning point on the transient part of the measured current;
using the identified turning point to determine the measurement point that is to be used for determining the diffusion feature, wherein the measurement point is offset in time from the turning point ($t_{turn}+\Delta t$, =identified point); and
using the measurement point current and its associated test time to determine simultaneously the diffusion feature and contribution of at least one redox-active substance.

2. A method as claimed in claim 1 further comprising storing calibration information and using the calibration information together with the measurement point in the measured current and its associated test time to determine the diffusion feature.

3. A method as claimed in claim 2 further comprising storing a function that relates a test time and the diffusion feature and using the function together with the measurement point current and its associated test time to determine the diffusion feature.

4. A method as claimed in claim 3, wherein the diffusion feature is a diffusion property or characteristic associated with mass transfer in a fluidic sample, including diffusion coefficient, haematocrit, or viscosity.

5. A method as claimed in claim 4 wherein the redox-active substance is at least one substance which undergoes redox reaction at the second electrode under the applied electric potential.

6. A method as claimed in claim 5, wherein the electric potential has a constant magnitude, or a varying magnitude with time, or combination of a constant magnitude and a varying magnitude.

7. A method as claimed in claim 6, wherein the current is a single value of the measured current, or an average value of consecutive measured currents over a duration of 0.03 second.

8. A method as claimed in claim 7, wherein the electrodes are configured in a co-facial manner such that the two electrode surfaces are spatially arranged facing each other with a minimum face-to-face distance of 10 to 1000 microns.

9. A method as claimed in claim 7, wherein the electrodes are configured in a co-planar manner such that the two electrode surfaces are spatially arranged in the same plane with the minimum edge-to-edge distance of 10 to 2000 microns.

10. A method as claimed in claim 7, wherein the electrodes are configured in a co-facial manner such that the two electrode surfaces are spatially arranged facing each other with a minimum face-to-face distance of 35 to 500 microns.

11. A method as claimed in claim 7, wherein the electrodes are configured in a co-facial manner such that the two electrode surfaces are spatially arranged facing each other with a minimum face-to-face distance of 50 to 120 microns.

12. A method as claimed in claim 7, wherein the electrodes are configured in a co-planar manner such that the two electrode surfaces are spatially arranged in the same plane with the minimum edge-to-edge distance of 50 to 900.

13. A method as claimed in claim 7, wherein the electrodes are configured in a co-planar manner such that the two electrode surfaces are spatially arranged in the same plane with the minimum edge-to-edge distance of 100 to 500 microns.

14. A method as claimed in claim 6, wherein the current is a single value of the measured current, or an average value of consecutive measured currents over a duration of 0.1 second.

15. A method as claimed in claim 6, wherein the current is a single value of the measured current, or an average value of consecutive measured currents over a duration of 0.5 second.

* * * * *